US009918762B2

(12) United States Patent
Federspiel et al.

(10) Patent No.: US 9,918,762 B2
(45) Date of Patent: Mar. 20, 2018

(54) SYSTEM FOR DEFORMING PLATE MEMBERS ON BONE

(71) Applicant: Acumed LLC, Hillsboro, OR (US)

(72) Inventors: Joshua P. Federspiel, Portland, OR (US); Stephanie C. M. Barnes, Portland, OR (US); Devan H. Jaecker, Beaverton, OR (US); Ryan C. Stafford, Sherwood, OR (US); Blake A. Matsuzaki, Renton, WA (US)

(73) Assignee: Acumed LLC, Hillsboro, OR (US)

( * ) Notice: Subject to any disclaimer, the term of this patent is extended or adjusted under 35 U.S.C. 154(b) by 320 days.

(21) Appl. No.: 14/850,869

(22) Filed: Sep. 10, 2015

(65) Prior Publication Data
US 2016/0310179 A1    Oct. 27, 2016

Related U.S. Application Data

(60) Provisional application No. 62/151,944, filed on Apr. 23, 2015.

(51) Int. Cl.
*A61B 17/80* (2006.01)
*A61B 17/88* (2006.01)

(52) U.S. Cl.
CPC ...... *A61B 17/8085* (2013.01); *A61B 17/8863* (2013.01); *A61B 17/8866* (2013.01)

(58) Field of Classification Search
CPC .................. A61B 17/8085; A61B 17/8863
See application file for complete search history.

(56) References Cited

U.S. PATENT DOCUMENTS

| 5,564,302 | A | * | 10/1996 | Watrous | A61B 17/8863 |
| | | | | | 72/458 |
| 5,651,283 | A | * | 7/1997 | Runciman | A61B 17/8863 |
| | | | | | 72/390.4 |
| 7,189,237 | B2 | | 3/2007 | Huebner | |
| 8,419,745 | B2 | | 4/2013 | Sixto, Jr. et al. | |
| 8,439,955 | B2 | | 5/2013 | Sixto, Jr. et al. | |
| 8,512,385 | B2 | | 8/2013 | White et al. | |
| 8,518,088 | B2 | | 8/2013 | Castaneda et al. | |
| 8,551,107 | B2 | | 10/2013 | Ng et al. | |
| 8,758,414 | B2 | | 6/2014 | Ng et al. | |

(Continued)

OTHER PUBLICATIONS

Thomas, Shane, Authorized Officer, U.S. Receiving Office, "International Search Report" in connection with related International Application No. PCT/US2015/049514, dated Dec. 11, 2015, 2 pages.

(Continued)

*Primary Examiner* — Christian Sevilla
(74) *Attorney, Agent, or Firm* — Kolisch Hartwell, P.C.

(57) ABSTRACT

System, including methods and apparatus, for deforming a plate member on bone. In some embodiments, the system may comprise a plate member defining a plurality of openings to receive fasteners that attach the plate member to bone. The plate member may include a pair of undercut flanges formed by opposite edge regions of the plate member. The system also may comprise a bending tool configured to be operatively associated with the plate member after the plate member is attached to bone, with a region of the bending tool positioned under each of the undercut flanges, such that rotation of the bending tool applies a moment to the plate member.

19 Claims, 12 Drawing Sheets

(56) References Cited

U.S. PATENT DOCUMENTS

| | | |
|---|---|---|
| 8,858,562 B2 | 10/2014 | Orbay et al. |
| 2002/0147450 A1 | 10/2002 | LeHuec et al. |
| 2004/0102777 A1* | 5/2004 | Huebner ............ A61B 17/1728 606/281 |
| 2007/0233111 A1 | 10/2007 | Orbay et al. |
| 2010/0069973 A1 | 3/2010 | Castaneda et al. |
| 2011/0092981 A1 | 4/2011 | Ng et al. |

OTHER PUBLICATIONS

Thomas, Shane, Authorized Officer, U.S. Receiving Office, "Written Opinion of the International Searching Authority" in connection with related International Application No. PCT/US2015/049514, dated Dec. 11, 2015, 9 pages.

\* cited by examiner

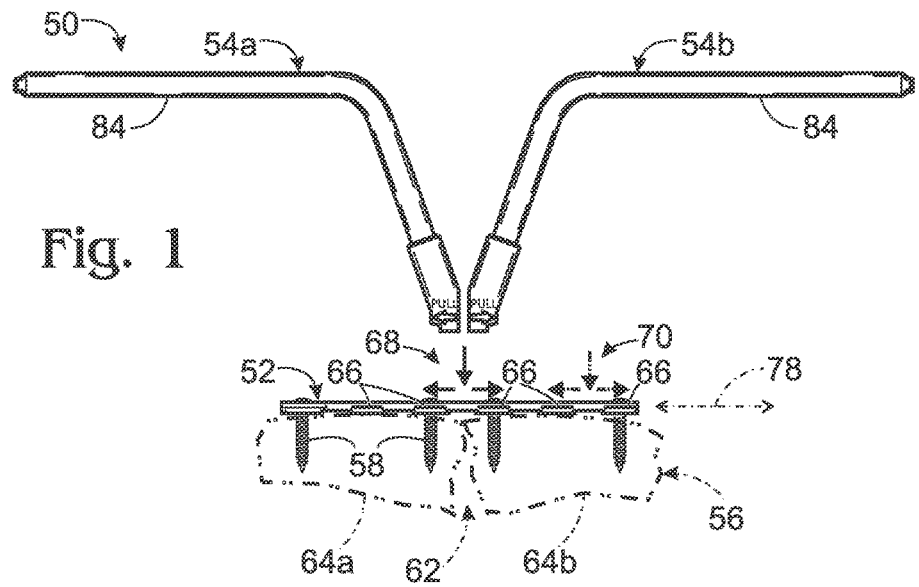
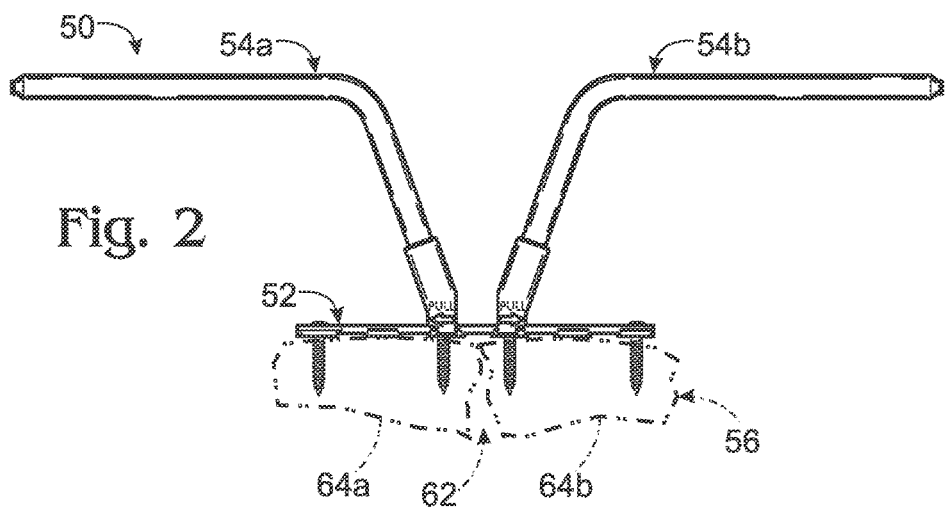
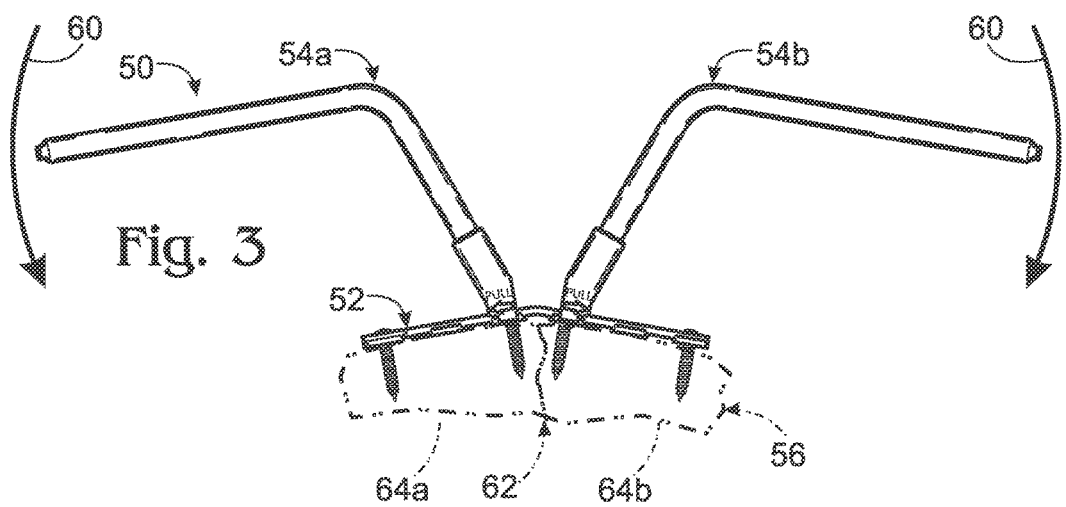

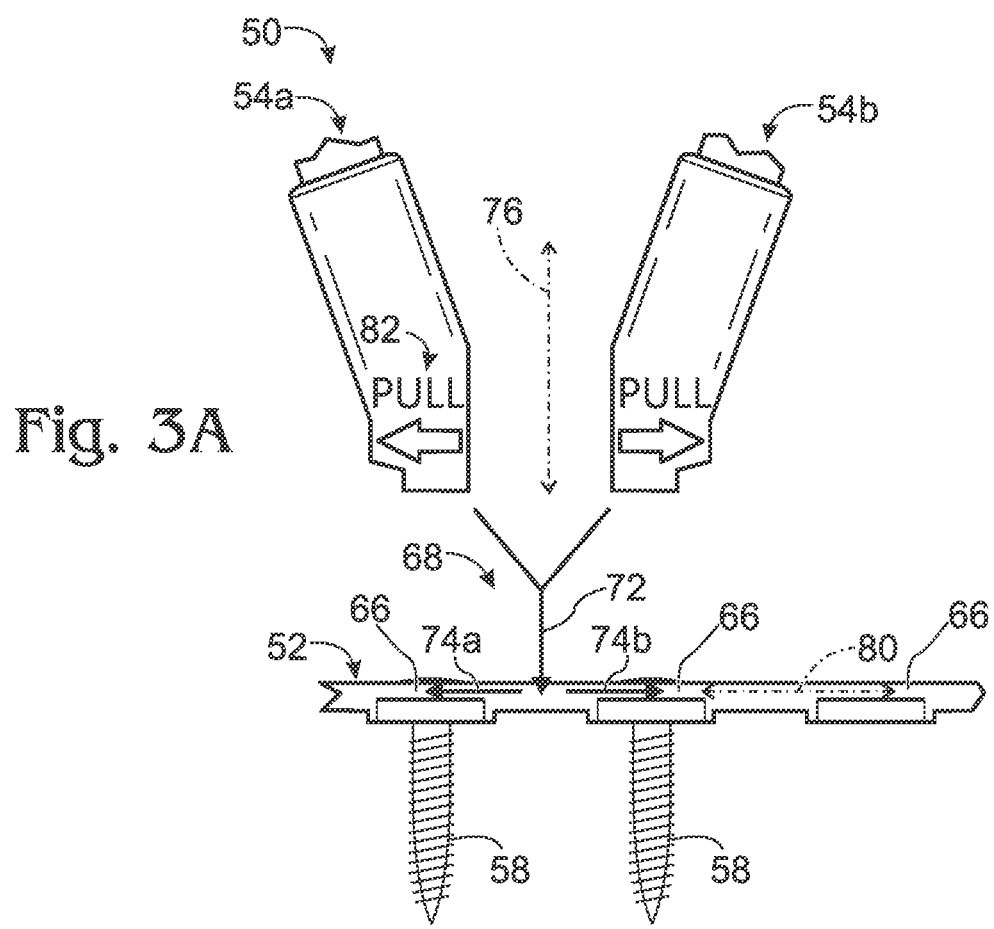

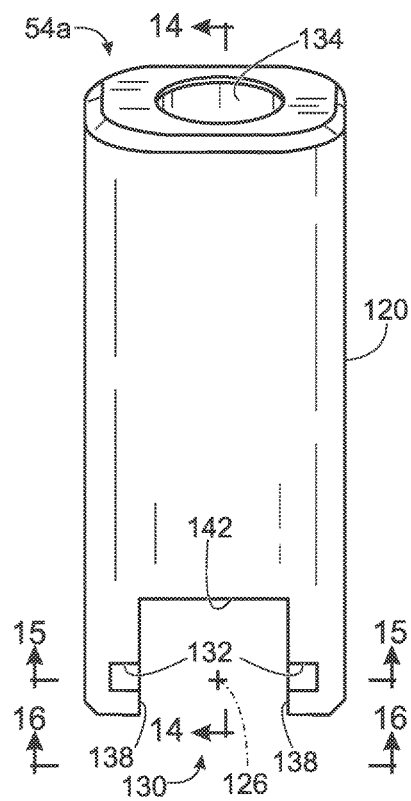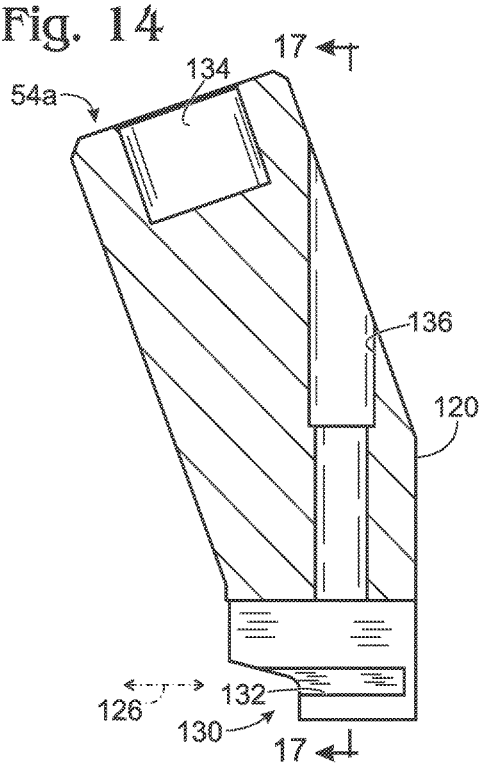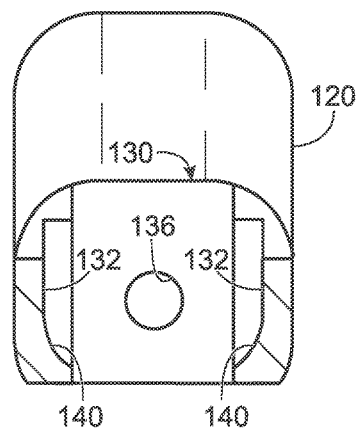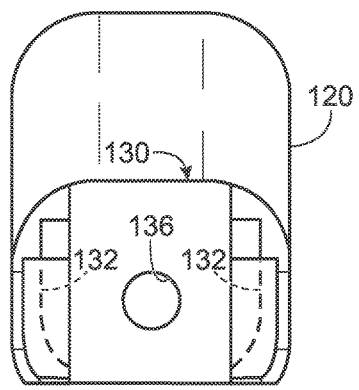

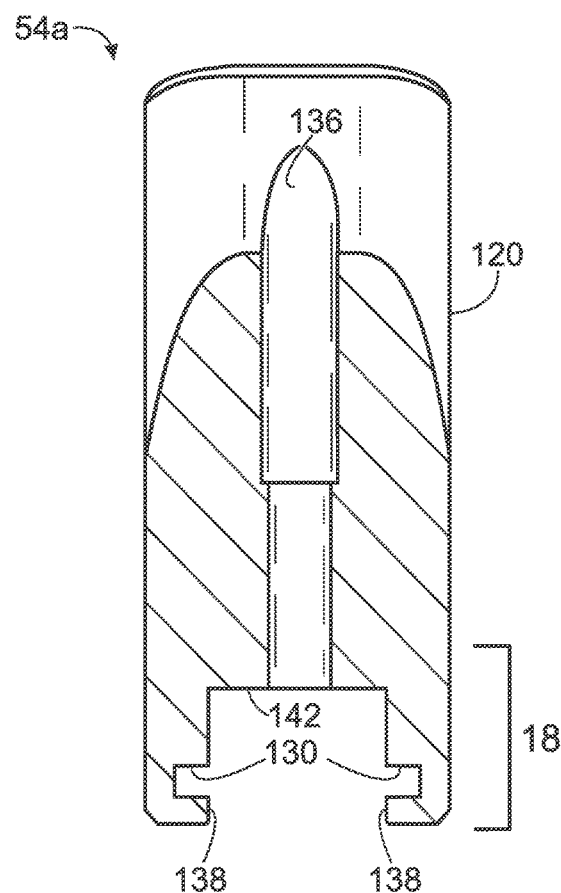
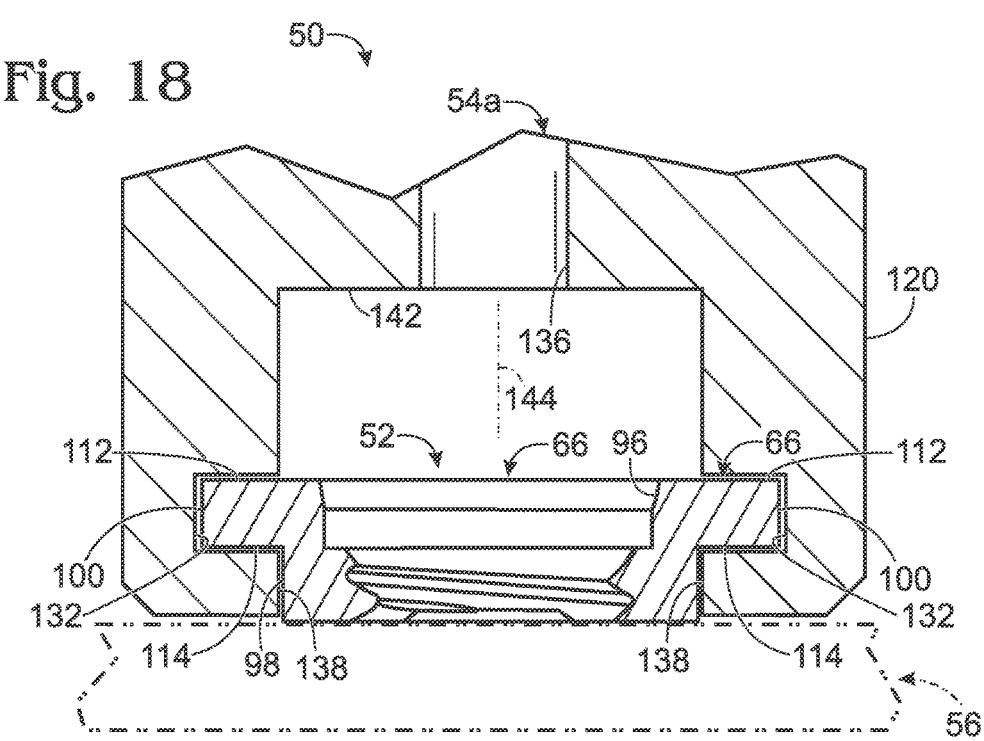

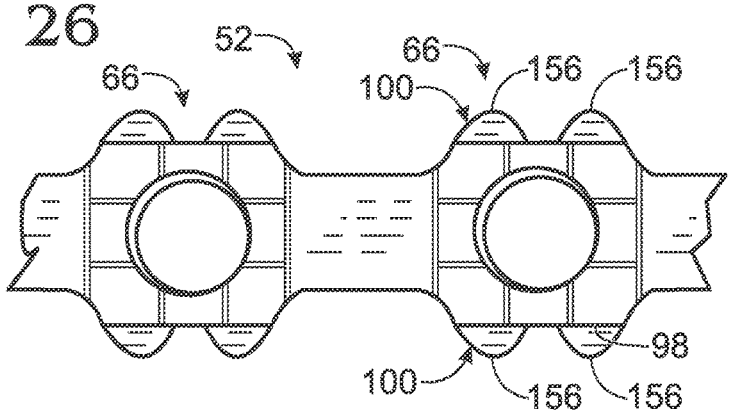
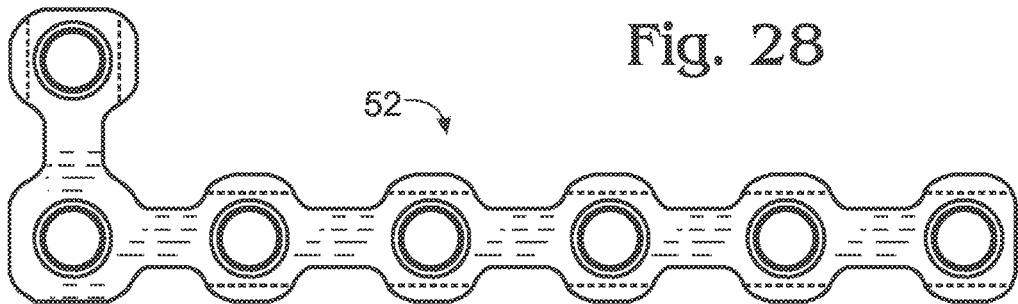

US 9,918,762 B2

SYSTEM FOR DEFORMING PLATE MEMBERS ON BONE

CROSS-REFERENCE TO PRIORITY APPLICATION

This application is based upon and claims the benefit under 35 U.S.C. § 119(e) of U.S. Provisional Patent Application Ser. No. 62/151,944, filed Apr. 23, 2015, which is incorporated herein by reference in its entirety for all purposes.

INTRODUCTION

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton.

To ensure that the skeleton retains its ability to perform its important functions, and to reduce pain and disfigurement, fractured bones should be repaired promptly and properly. Typically, fractured bones are treated using fixation devices, which reinforce the fractured bones and keep them aligned during healing. Bone plates are implanted fixation devices that are mounted to bone with fasteners, such as bone screws, with the bone plate generally spanning at least one fracture or other discontinuity in the bone.

A major challenge in bone fixation, particularly with comminuted fractures (i.e., fractures in which the bone is broken, splintered, or crushed into a number of pieces), is to reduce the fractures by moving fragments of the bone toward their pre-fracture positions. In many cases, relatively small changes to where each fragment is located and how the fragment is oriented can make a large difference in the overall reconstruction of a fractured bone and thus the degree to which the function of the bone is restored. However, it can be very difficult for a surgeon to manipulate bone fragments so that the fractures are properly reduced. Furthermore, the surgeon may be frustrated by the tendency of the bone fragments to move out of position as the fragments are being secured to a bone plate with fasteners.

Fracture reduction can be adjusted and improved by bending the bone plate in situ after the plate is attached to bone. Bending can be enabled with bending rods coupled to the bone plate to create graspable levers for applying a bending moment to the bone plate. The bending rods can be threaded into openings of the bone plate to attach the rods directly to the bone plate, or may be slidably mated with guide tubes that protrude from openings of the bone plate. With either approach, openings of the bone plate recruited to receive the bending rods or guide tubes cannot be occupied by bone screws while the bending rods or guide tubes interface with these openings.

The reliance on bone plate openings to interface with bending equipment has various disadvantages. For example, this reliance limits where the bone plate can be secured to bone with bone screws before bending. The surgeon generally must predict which openings of the bone plate are likely to interface with bending equipment, and leave those openings unoccupied and available for a bending procedure. If the prediction is not accurate, the surgeon may need to remove one or more bone screws before the bending procedure, and then re-install those bone screws after the procedure has been completed.

Better approaches are needed to bend a bone plate in situ, while the bone plate remains attached to bone.

SUMMARY

The present disclosure provides a system, including methods and apparatus, for deforming a plate member on bone. In some embodiments, the system may comprise a plate member defining a plurality of openings to receive fasteners that attach the plate member to bone. The plate member may include a pair of undercut flanges formed by opposite edge regions of the plate member. The system also may comprise a bending tool configured to be operatively associated with the plate member after the plate member is attached to bone, with a region of the bending tool positioned under each of the undercut flanges, such that rotation of the bending tool applies a moment to the plate member.

BRIEF DESCRIPTION OF THE DRAWINGS

FIG. 1 is an exploded view of an exemplary in situ bending system prior to assembly and including a bone plate secured to a fractured bone (in phantom outline) with a plurality of bone screws, and also including a pair of bending tools configured to be operatively associated with the bone plate (and/or a plate member thereof), in accordance with aspects of the present disclosure.

FIG. 2 is an assembled view of the system of FIG. 1 taken before the bone plate has been deformed by application of a bending moment to the bone plate with the bending tools.

FIG. 3 is another assembled view of the system of FIG. 1, taken as in FIG. 2 but after the bone plate has been deformed by the bending tools.

FIG. 3A is a fragmentary, exploded view of the system of FIG. 1.

FIG. 13 is an elevation view of the mating portion of FIG. 12.

FIG. 14 is a sectional view of the mating portion of FIG. 12 taken generally along line 14-14 of FIG. 13.

FIG. 15 is another sectional view of the mating portion of FIG. 12, taken generally along line 15-15 of FIG. 13.

FIG. 16 is a bottom view of the mating portion of FIG. 12, taken generally along line 16-16 of FIG. 13.

FIG. 17 is still another sectional view of the mating portion FIG. 12, taken generally along line 17-17 of FIG. 14.

FIG. 18 is a fragmentary sectional view of the mating portion of FIG. 12 mated with the bone plate of FIG. 1, taken generally around the region indicated at "18" in FIG. 17, and with the bone plate attached to a bone (in phantom outline).

FIG. 26 is a fragmentary bottom view of another exemplary bone plate for the bending systems of the present disclosure.

FIGS. 27-29 are top views of other exemplary bone plates for the bending systems of the present disclosure.

DETAILED DESCRIPTION

Figure 4:
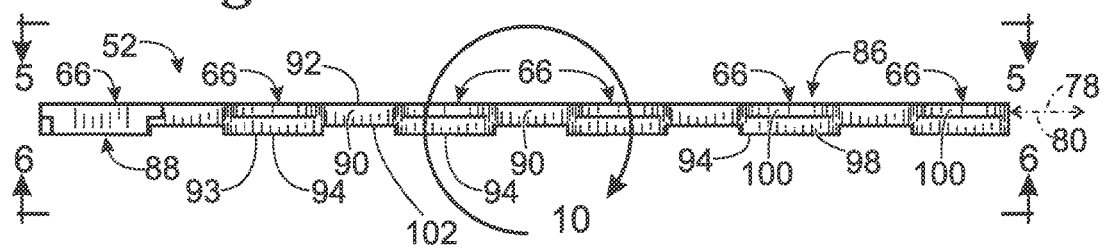
FIG. 4 is an elevation view of the bone plate of FIG. 1, taken from a position lateral to the bone plate as in FIG. 1 but in the absence of other system components.

The present disclosure provides a system, including methods and apparatus, for deforming a plate member on bone. In some embodiments, the system may comprise a plate member defining a plurality of openings to receive fasteners that attach the plate member to bone. The plate member may include a pair of undercut flanges formed by opposite edge regions of the plate member. The system also may comprise a bending tool configured to be operatively associated with the plate member after the plate member is attached to bone, with a region of the bending tool positioned under each of the undercut flanges, such that rotation of the bending tool applies a moment to the plate member.

Further aspects of the present disclosure are described in the following sections: (I) overview of an exemplary bending system for bone plates, (II) bone plates, (III) bending tools, (IV) methods of bone fixation with a bending system, and (V) examples.

I. OVERVIEW OF AN EXEMPLARY BENDING SYSTEM FOR BONE PLATES

This section provides an overview of an exemplary system 50 for deforming a bone plate 52 in situ (on bone); see FIGS. 1-3 and 3A.

System 50 may include one or more bending tools, such as tools 54*a* and 54*b*. The tools may be operatively associated with bone plate 52 (and/or a plate member thereof) after (or before) the bone plate (and/or the plate member) has been attached to a bone 56 with one or more fasteners 58, such as bone screws (compare FIGS. 1 and 2). Once the tools are assembled with the bone plate (and/or plate member thereof), the surgeon may manipulate the bending tools, indicated by arrows at 60, to apply a bending moment to bone plate 52 that deforms the bone plate and/or plate member (compare FIGS. 2 and 3). Bending tools 54*a* and 54*b*, and/or plate-mating portions thereof, may (or may not) be copies of one another.

The bending tools may apply any suitable deforming force to the bone plate. For example, in the depicted embodiment, the tools are applying a bending moment about a traverse axis that is orthogonal to the long axis of the bone plate.

Deformation (interchangeably termed bending) of the bone plate may improve reduction of a fracture. For example, the bone plate may span at least one discontinuity (e.g., a fracture 62) in the bone flanked by bone portions or fragments 64*a*, 64*b*. One or more fasteners 58 (such as threaded fasteners) may attach the bone plate to each of the bone portions. For example, in the depicted embodiment, two fasteners 58 extend from the bone plate into each bone portion 64*a* and 64*b*. Bending the bone plate may move bone portions 64*a*, 64*b* closer to their pre-fracture positions within bone 56 (compare FIGS. 2 and 3).

Bending tools 54*a*, 54*b* may be assembled with the bone plate over pre-installed fasteners 58 (compare FIGS. 1 and 2), even fasteners with heads protruding above the top surface of the bone plate. Accordingly, the surgeon is free to install fasteners 58 in any desired combination of bone plate openings before the bone plate is assembled with tools 54*a*, 54*b*. Furthermore, each of the bending tools may be interchangeably assembled with the bone plate at each of a plurality of spaced association sites 66, to allow the bone plate to be bent as desired between any pair of the association sites, such as between any adjacent pair of association sites 66. As described in more detail below, each of association sites 66 may bracket (e.g., transversely bracket) an opening of the bone plate. This configuration may protect the openings (and particularly internal threads, if any, therein) from deformation during the bending process, if left unoccupied by the surgeon until a second round of fastener installation after deformation.

FIG. 1 shows two assembly routes 68, 70 composed of arrows indicating a pair of the various assembly configurations available to the surgeon for associating tools 54*a*, 54*b* with the bone plate. FIG. 3A shows a magnified, fragmentary version of selected aspects of FIG. 1, particularly assembly route 68, with the arrows of route 68 positioned more precisely. Each route 68 and 70 includes a pre-mating or aligning path 72 and a pair of respective mating paths 74*a*, 74*b* for tools 54*a*, 54*b*. Each pre-mating path 72 may extend along an orthogonal axis 76 transverse to a (global) long axis 78 defined by bone plate 52 and/or to a local long axis 80 defined by the bone plate locally near the selected association site 66. The local long axis interchangeably may be termed the direction of elongation of the bone plate (or plate member and/or plate portion thereof). In some embodiments, such as with a linear bone plate 52, global long axis 78 of the bone plate may be coextensive with each local long axis 80 defined near an association site, whereas with nonlinear plates, such as a longitudinally curved plate, the local long axes may not be coextensive with one another.

Movement of each tool along pre-mating path 72 may bring the tool into proximity or contact with the bone plate, such as a top surface thereof, and may position the tool with an axial offset from the selected association site 66, but in alignment therewith for subsequent mating. The tool then may be moved in a direction parallel to long axis 78 (and/or local long axis 80), on path 74a or 74b, to operatively mate the tool with the bone plate for subsequent application of deforming force to the bone plate. Path 74a or 74b also may be described as being parallel to edge regions or flanges of the association site and/or parallel to a plane defined by the bone plate (e.g., defined locally).

In the depicted embodiment, tools 54a and 54b are rotated 180 degrees relative to one another to allow movement in opposite directions, on respective paths 74a, 74b, for operative association with respective adjacent sites 66. Each tool may have visible indicia 82, such as an arrow and/or one or more alphanumeric characters (e.g., spelling a word such as "pull") to indicate the direction in which the tool is moved for mating with an association site 66. Furthermore, each tool may have a shaft 84 extending to a proximal end thereof in a direction of mating (see FIG. 1).

II. BONE PLATES

This section describes further aspects of bone plate 52 of FIG. 1; see FIGS. 4-10.

Bone plate 52 may be a single plate member or may be an assembly of two or more plate members, which may overlap one another. Each plate member may be or include a plate portion having one or more openings and edge regions for engagement with a bending tool(s). In some embodiments, bone plate 52 may include a main fixation plate (a primary plate member) and one or more discrete, optional, ancillary plate members having undercut flanges (also called wings) for engagement with a bending tool. In some embodiments, bone plate 52 may include a primary plate member and one or more ancillary plate members formed integrally with the primary plate member and having undercut flanges for engagement with a bending tool. Each plate member and/or plate portion may have a bone-contacting surface that is formed by a bottom/inner side of the plate member and is configured to contact bone. The plate member and/or plate portion has a plate geometry, with a thickness that is less than its width and length, such as less than 50% or 25% of the width and length.

Figure 5:
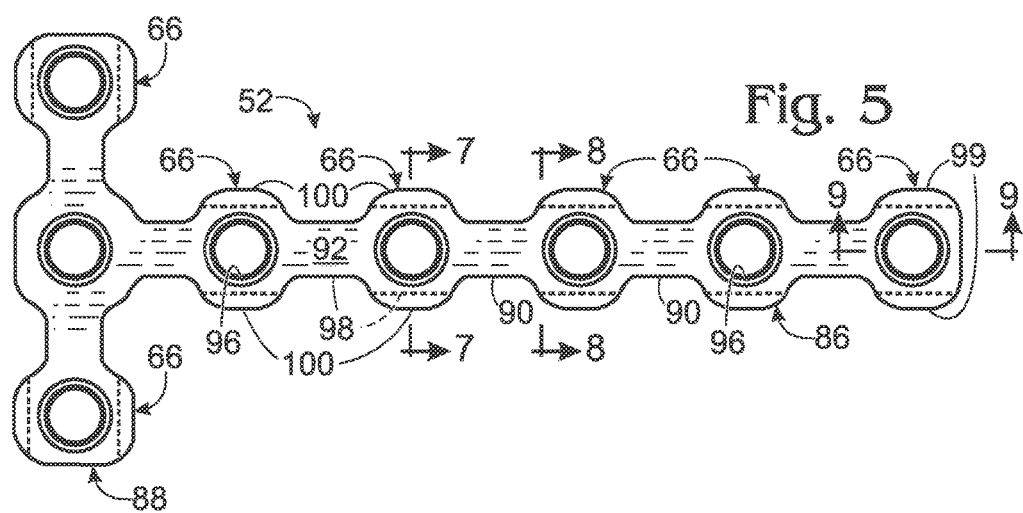
FIG. 5 is a plan view of the bone plate of FIG. 1, taken generally along line 5-5 of FIG. 4.
Figure 6:
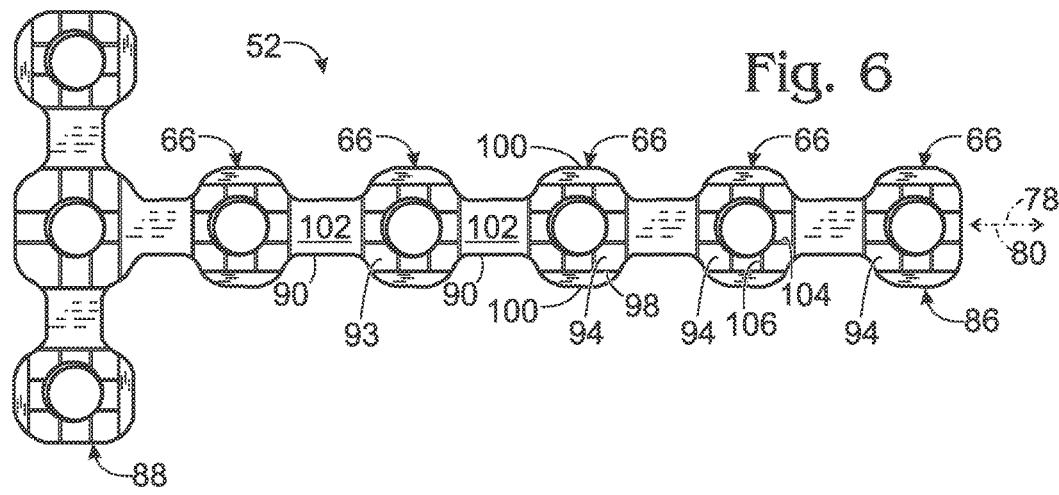
FIG. 6 is a bottom view of the bone plate of FIG. 1, taken generally along line 6-6 of FIG. 4.

FIGS. 4-6 show respective elevation, top, and bottom views of bone plate 52 of FIG. 1. The bone plate has a longitudinal portion 86 arranged on long axis 78 and a transverse portion 88 extending orthogonally in opposite orthogonal directions from long axis 78. Association sites 66 may be arranged along the longitudinal portion and/or the transverse portion of the bone plate. In other embodiments, the bone plate may lack transverse portion 88, the transverse portion may extend in only one orthogonal direction from long axis 78 and/or may extend obliquely with respect to long axis 78, and/or the longitudinal portion may extend along a longitudinally curved or angular path.

Bone plate 52 may have a varying (nonuniform) width along longitudinal portion 86 and/or along transverse portion 88. The bone plate may be wider at association sites 66 and narrower at webs 90 (interchangeably termed bridging regions) disposed intermediate each adjacent pair of association sites 66. Each web 90 may provide an access site for bringing bending tool 54a or 54b into alignment with a desired association site 66 of bone plate 52, for subsequent mating of the bending tool with the bone plate parallel to a local long axis of the bone plate and/or a plate member thereof.

The bone plate has a top side 92 opposite a bottom side 93. The top side forms an upper surface or outer surface that faces away from bone. The bottom side forms a lower surface or inner surface having one or more bottom surface regions 94 or inner surface regions that face toward and contact bone. Bottom surface regions 94 may be separated from one another by recessed regions of the bottom surface formed by webs 90, as described below. To simplify the description, the bone plate is described herein with the top side and the bottom side each at least generally orthogonal to the direction of gravity and facing up and down, respectively, and with the bone plate attached or attachable to an at least generally horizontal bone surface that faces up. However, the bone plate may be attached to any suitable bone surface with any suitable orientation with respect to gravity.

The bone plate may define a plurality of openings 96 each extending through the bone plate from top side 92 to bottom side 93. Each opening may receive a fastener that attaches the bone plate to bone and may or may not have structure, such as an internal thread, for attaching the fastener to the bone plate. The openings may be arranged along longitudinal portion 86 and/or transverse portion 88 of the bone plate.

Bone plate 52 may have a body 98 and edge structure 99 formed by at least a pair of undercut flanges 100 projecting from the body at each association site 66. Each flange may include one or more protrusions (also see Section V). The flanges may be formed by opposite edge regions of the bone plate and each may be elongated parallel to a local long axis defined by the bone plate near the flanges, and parallel to a mating axis along which the bending tool is mated with the association site. The local long axis may be disposed intermediate the flanges. The flanges may project in opposite directions relative to one another (to form a pair of "wings"), away from local long axis 80 (and/or global long axis 78) defined by body 98, at and adjacent the association site. The flanges may bracket an opening 96 defined by the association site. As described in more detail below, the flanges may be elevated with respect to bottom surface region(s) 94 of the bone plate and thus may be elevated from and may form an overhanging protrusion above bone when the bone plate is secured to the bone. The presence of undercut/elevated flanges 100 allows a region (e.g., a tool flange or ridge) of the bending tool to be received under each plate flange, between an underside of the plate flange and bone, such that the bending tool is coupled to the bone plate for application of a bending moment.

The majority of the bone plate may be formed by body 98. The body may extend continuously along the length of the bone plate and may provide the central supporting portion of each association site 66, may form each web 90, and may define each opening 96. Flanges 100 may be formed integrally with body 98 and may be continuous with the body. In other examples, the flanges may be provided by separate appendages attached removably to the body of the bone plate (e.g., see Section V).

Bottom side 93 of bone plate 52 may be composed of various surface regions (see FIGS. 4 and 6). Webs 90 may be elevated with respect to bottom surface regions 94 to create recessed, lower web surface regions 102 (see FIG. 4), which may be spaced slightly from bone. The bone plate may be stronger at association sites 66 than webs 90. In other words, the webs may provide sections at which the bone plate is relatively more flexible and easily bent, by being narrower and/or thinner than at interspersed association sites 66. This geometry helps to protect each association site 66 from deformation when the bone plate is being bent. Deformation of an association site is generally undesirable because it can deform the internal thread of opening 96 within the association site.

The bottom side of bone plate 52 also may define one or more longitudinal recesses 104 and a plurality of transverse recesses 106, which also may be spaced slightly from bone (see FIG. 6 and below). Recesses 104 and 106 may create a plurality of bone-contacting bottom surface regions 94 (here, four) for each association site 66.

Figure 7:
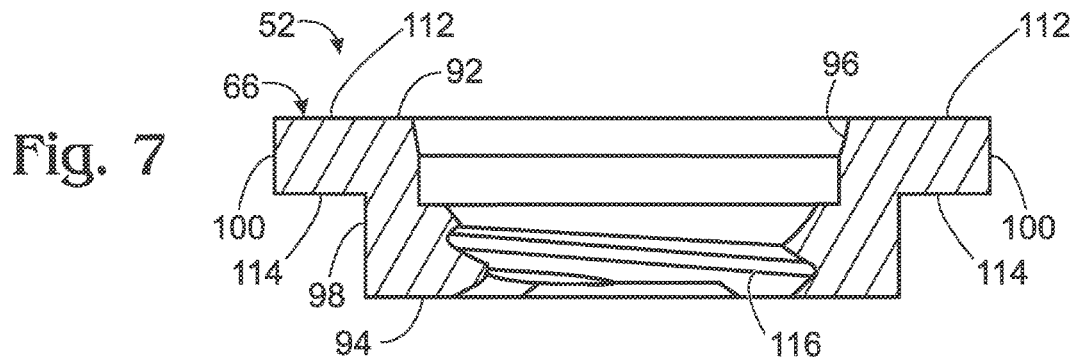
FIG. 7 is a cross-sectional view of the bone plate of FIG. 1, taken generally along line 7-7 of FIG. 5.

FIG. 7 shows a cross-sectional view of bone plate 52 taken through one of association sites 66. Flanges 100 each may project orthogonally from the bone plate to form an overhang having an upper side 112 and an underside 114. The flange may be described as being undercut, whether or not the flange is created by a cutting process. The bending tool may be received on each flange for contact with at least underside 114, and optionally upper side 112, of the flange. Underside 114 may be horizontal, sloped, curved, or a combination thereof, among others (also see Section V). Accordingly, the cross section of the bone plate at an association site may be T-shaped, dovetail-shaped, laterally grooved, or the like.

Opening 96 may have an internal thread 116 for attaching an externally threaded fastener to the bone plate at the opening. An upper region of the opening may widen to receive at least a lower portion of a head of the fastener.

Figure 8:
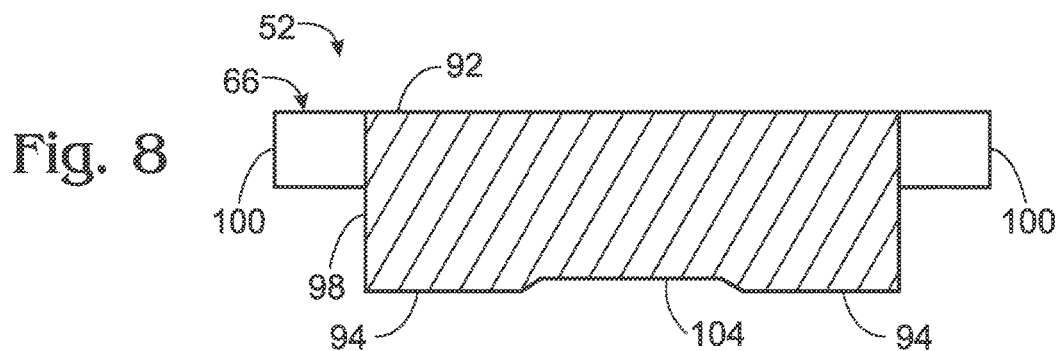
FIG. 8 is another cross-sectional view of the bone plate of FIG. 1, taken generally along line 8-8 of FIG. 5.

FIG. 8 is a cross-sectional view of bone plate 52 taken at an end of an association site 66. Longitudinal recess 104 formed by the bottom side of the bone plate is disposed intermediate bottom surface regions 94.

Figure 9:
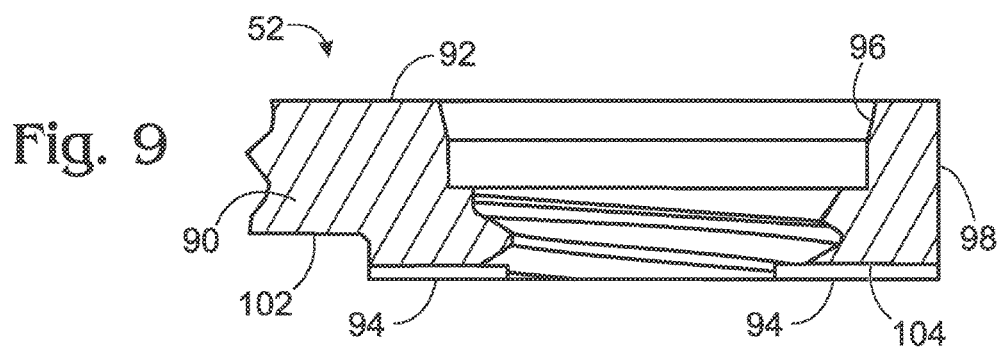
FIG. 9 is a fragmentary, longitudinal sectional view of the bone plate of FIG. 1, taken generally along line 9-9 of FIG. 5.
Figure 10:
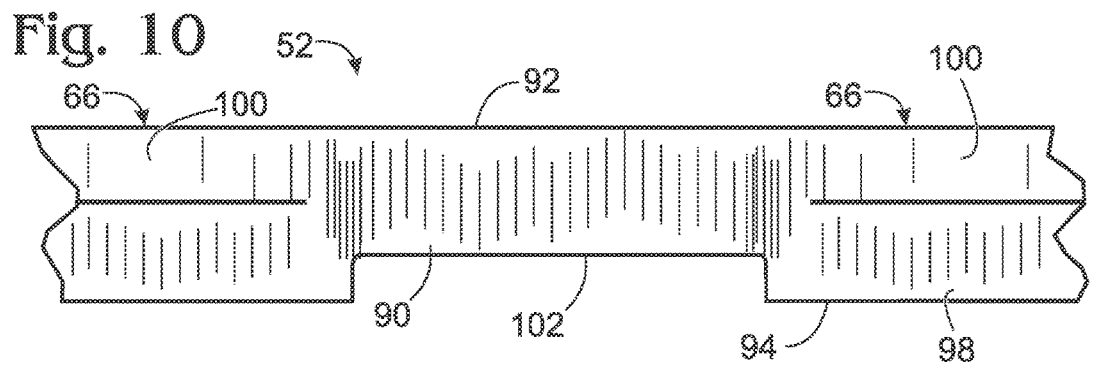
FIG. 10 is a fragmentary elevation view of the bone plate of FIG. 1, taken generally around the region indicated at "10" in FIG. 4.
Figure 11:
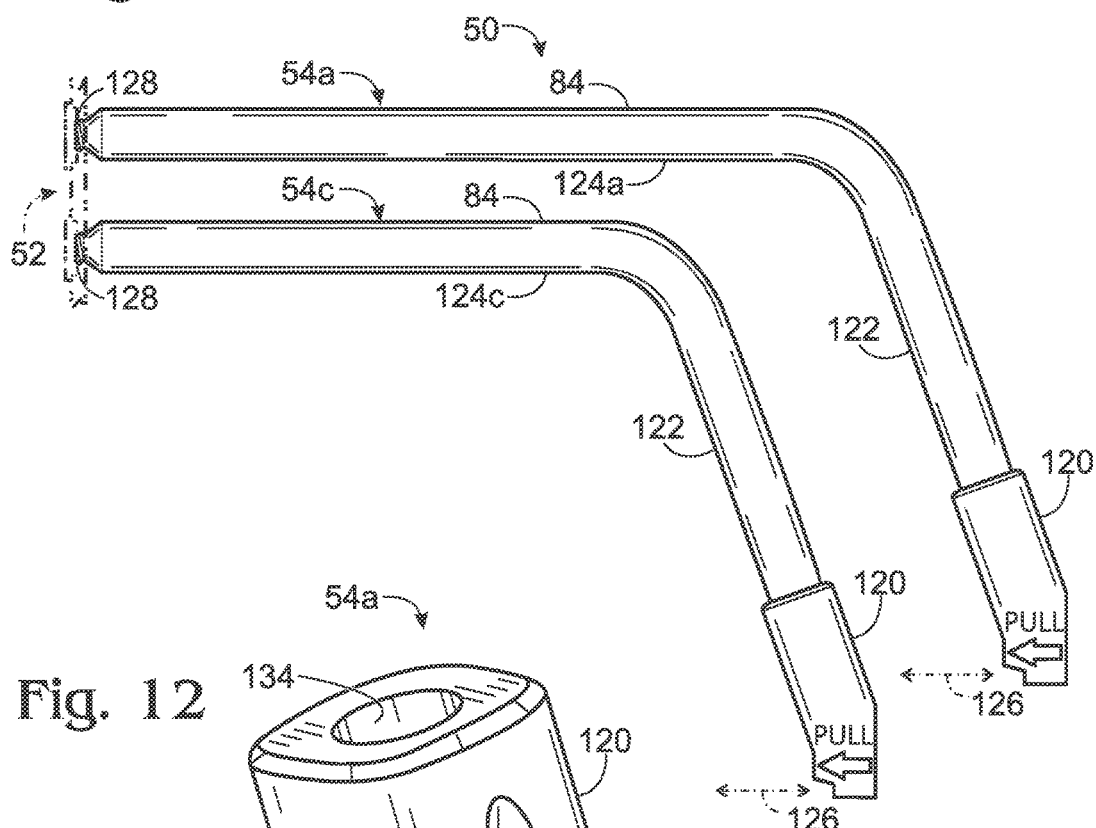
FIG. 11 is side view of an exemplary pair of bending tools for the system of FIG. 1.

FIGS. 9 and 10 show respective sectional and fragmentary views of bone plate 52. Web 90 may be elevated from bottom surface regions 94 to form recessed surface region 102.

The bone plates may be deformed irreversibly and thus may be formed of any plastically deformable material. In some embodiments, the bone plates may be formed of a biocompatible metal (such as stainless steel, titanium or an alloy thereof, or the like) or a biocompatible plastic, among others.

Further aspects of exemplary bone plates for the bending systems are described elsewhere herein, such as in Section V, among others.

III. BENDING TOOLS

This section describes further aspects an exemplary pair of bending tools 54a, 54c for system 50 of FIG. 1; see FIGS. 11-18.

Tools 54a and 54c each have a mating portion 120 to interface with bone plate 52, and a shaft 84 mounted at an upper end of the mating portion. The mating portions 120 of the pair of tools may be copies of one another, but shafts 84 may (or may not) be different, as shown here, to facilitate use of either end of the tools for operative association with the bone plate.

Each shaft 84 may be graspable to facilitate manipulation of the tool during connection to the bone plate, subsequent application of a deforming force, and then removal from the bone plate. The shaft may be nonlinear to form a distal end portion 122 that extends to mating portion 120 and a proximal end portion 124a or 124c extending parallel to a mating axis 126 defined by mating portion 120. Mating axis 126 may be arranged parallel to the local long axis of the bone plate when the tool is mated with an association site 66 of the bone plate to operatively associate the tool with the bone plate.

The proximal end of each proximal end portion 124a or 124c may include an external thread 128 that is complementary to the internal threads of openings 96 of bone plate 52 (shown as fragmentary in phantom outline). Accordingly, each tool 54a, 54c provides the option of operatively associating either end with the bone plate near or at a desired bone plate opening 96, if the opening is not currently occupied by a fastener. Proximal end portions 124a, 124c may be of different length to permit both tools to be threaded into respective openings 96 of the bone plate without interference from one another. For example, in the depicted embodiment, thread 128 of shorter tool 54c may be threaded into an opening 96 first, and then thread 128 of longer tool 54a may be threaded into another opening 96 of the bone plate. The greater length of proximal end portion 124a positions distal end portion 122 and mating portion 120 of longer tool 54a farther from bone plate 52 than the corresponding parts of tool 54c, allowing tool 54a to be rotated freely while being threaded into an opening 96, without any obstruction from tool 54c.

Figure 12:
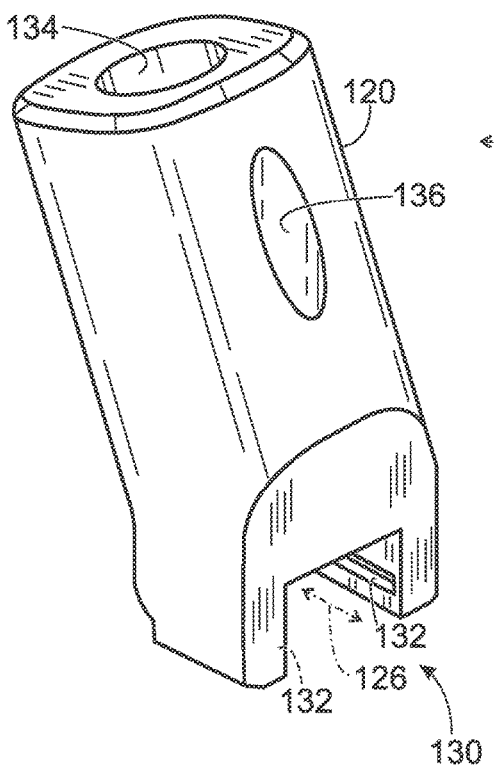
FIG. 12 is a view of a mating portion from a bending tool of FIG. 11, taken in the absence of the shaft of the tool.

FIG. 12 shows further aspects of mating portion 120 of tool 54a. The mating portion, which may be formed integrally with or separately from shaft 84 of the tool, may define a receiving region 130 that interfaces with and is at least partially complementary to association site 66 of bone plate 52. The receiving region 130 may include a pair of tracks 132, such as grooves and/or ridges/flanges, each extending parallel to one another and parallel to mating axis 126. The tracks guide mating portion 120 onto flanges 100 of an association site 66 and may have walls that contact the upper side and/or the underside of each flange after mating and particularly during plate deformation. Mating portion 120 also may define a socket 134 to receive an end of shaft 84 of the tool. The mating portion further may define a guide channel 136 that is arranged coaxially with an opening 96 of bone plate 52 after the mating portion has been fully mated with an association site 66 of the bone plate. The guide channel may receive the leading end region of a drill and guide the drill through opening 96 and into underlying bone to form a hole in the bone. A fastener may be placed into the hole after (or before) the mating portion is removed from the bone plate.

FIGS. 13-18 show additional views of mating portion 120 of bending tool 54a alone or after mating with an association site 66 of bone plate 66 (see FIG. 18). Receiving region 130 may form a pair of hooks 138 (interchangeably called flanges) that create tracks 132 (see FIGS. 13, 14, 17, and 18). The hooks may extend under flanges 100 when the tool is mated with the bone plate. One or both tracks 132 may have a stop region 140 that blocks advancement of tracks 132 onto flanges 100 (see FIG. 15). For example, in the depicted embodiment, each track 132 is a groove having a blind end that flange 100 contacts to place the tool at a predetermined position along one of the association sites (e.g., to align guide channel 136 with an underlying opening 96 of bone plate 52. Alternatively, each track 132 may be a groove that is open at each end, and flange 100 may have a stop region that prevents further travel of the mating portion along the mating axis when fully mated.

FIGS. 13, 17, and 18 show a void 142 defined by receiving region 130 of mating portion 120. The void may be large enough to receive association site 66 of the bone plate and a head of a fastener that may be protruding above the top side of the bone plate.

FIG. 18 shows an exemplary complementary relationship between flanges 100, tracks 132, and hooks/flanges 138. Flanges 100 may be received in tracks 132, to position upper sides 112 of flanges 100 adjacent and under an upper wall region of the tracks and to position undersides 114 of flanges 100 adjacent and over a lower wall region of the tracks. Rotation of tool 54a may cause mating portion 120 to bear against both the upper side and the underside of each flange, particularly when the rotation is about an axis orthogonal to the long axis of the bone plate, to apply a moment to the bone plate at association site 66.

Bone plate 52 is attached to a bone 56, which is shown in phantom outline in FIG. 18. Each plate flange 100 is spaced from bone 56, with tool flanges 138 disposed between plate flanges 100 and the bone. The bottom side of tool 54a may be flush with the bottom side of the bone plate or may be elevated with respect to the bottom side, as shown, to minimize contact between the tool and the bone when the tool is being mated with the bone plate.

The coaxial arrangement of drill guide channel 136 and opening 96 is shown in FIG. 18. The channel and the opening are both centered on a same axis 144.

Further aspects of bending tools are described elsewhere herein, such as in Section V.

IV. METHODS OF BONE FIXATION WITH A BENDING SYSTEM

This section describes exemplary methods of bone fixation with the bending system of the present disclosure. The steps described in this section may be performed in any suitable order and combination and may be combined with or modified by any other steps, elements, and/or features of the present disclosure.

At least one bone to be fixed may be selected. The bone may be any suitable bone of a vertebrate species, such as humans. Exemplary bones that may be selected include at least one bone of the arms (e.g., a humerus, radius, or ulna), the legs (e.g., a femur, tibia, or fibula), the hands/wrists (e.g., a carpal, metacarpal, or phalange), the ankles/feet (e.g., a tarsal, metatarsal, or phalange), the pelvis, the spinal cord (vertebrae), the rib cage (e.g., a rib or sternum), the skull (e.g., a cranial bone or facial bone), a scapula, a clavicle, or the like.

The selected bone(s) may have any suitable condition that would benefit from stabilization by fixation. Exemplary conditions of the selected bone(s) may include a discontinuity, such as at least one fracture, a cut (e.g., created during an osteotomy procedure), a nonunion, a joint between two bones (for a bone fusion procedure), a structural weakness, or the like.

A bone plate including at least one plate member may be selected for fixing the selected bone. The plate member may be a primary fixation device for the bone or may be an ancillary fixation device. In some examples, the bone may have a comminuted fracture that breaks the bone into more than two pieces. Two or more larger pieces of the bone may be fixed relative to one another with a primary fixation plate or nail, among others, and two or more smaller pieces of the bone may be fixed relative to one another with the selected bone plate.

The selected bone plate (and/or plate member thereof) may have any suitable shape. The bone plate and/or plate member may be linear, angular (e.g., H-shaped, L-shaped, T-shaped, X-shaped, Y-shaped, etc.), curved (e.g., longitudinally curved in plane or out of plane), a combination thereof, or the like. The bone plate and/or plate member may be deformed, such as by the surgeon, before the bone plate and/or plate member is attached to the selected bone, to improve the fit to bone. The bone plate and/or plate member also or alternatively may be cut or broken to decrease the size of the bone plate and/or plate member.

The selected bone plate and/or plate member may be secured to one or more pieces of the bone with one or more fasteners, such as at least one fastener or two or more fasteners extending into and/or around each piece of the one or more pieces of the bone. Exemplary fasteners that may be suitable include threaded fasteners (bone screws), pins, wires, sutures, rivets, or the like. Threaded fasteners may be disposed in threaded engagement with a piece of the bone and, optionally, with the bone plate and/or plate member, too. Any suitable number of openings of the bone plate and/or plate member (including every opening) may be occupied by fasteners after the bone plate and/or plate member is secured to the bone, and before the bone plate and/or plate member is deformed with the bending system of the present disclosure.

One or more bending tools may be operatively associated with the bone plate and/or plate member for transmission of a deforming moment to the bone plate and/or plate member. In some examples, a pair of bending tools may be associated with the bone plate (and/or plate member), such as associated serially or in parallel. A surgeon may select a pair of association sites for the bending tools, and then may mate a bending tool with each site. In some embodiments, both bending tools may be aligned with different association sites of the bone plate and/or plate member via the same access site of the bone plate (or plate member). The access site may permit each of the bending tools to be positioned for mating with one of the association sites, by travel along the same axis orthogonal to a mating axis of the association site. Each bending tool may be mated with the association site in a direction parallel to the mating axis, which may be parallel to a local and/or global long axis of the bone plate (and/or plate member) and/or parallel to axes defined by edge regions/flanges of the association sites. The bending tools may mate with their respective association sites by movement in opposite directions along respective mating axes. The bending tools may be placed at predetermined positions along the bone plate and/or plate member by the mating of both tools with their respective association sites.

A bending moment may be applied to the bone plate and/or plate member by the bending tool(s). The bending moment may be applied by a surgeon manually to a shaft(s) of the bending tool(s). The bending moment may deform the bone plate and/or plate member about an axis parallel, orthogonal, and/or oblique to a local long axis of the bone plate (or plate member).

One or both of the bending tools may be removed from the bone plate and/or plate member. At least one of the bending tools then may be associated with the bone plate at one or more other association sites, if further bending is to be performed at one or more other positions along the bone plate (or plate member). Removal of each bending tool may be performed by moving the bending tool parallel to the mating axis, but in a direction opposite to that followed for mating, and then separating the bending tool from the bone plate (or plate member) along an axis transverse to the plane of the bone plate (or plate member).

At any suitable time during or after the bending procedure, one or more additional fasteners may be placed into bone from previously unoccupied openings of the bone plate (and/or plate member), to further attach the bone plate (or plate member) to bone. For example, a bending tool may guide a drill through an opening and into bone, and then a fastener may be placed into bone from the opening, before or after the bending tool is removed from the bone plate (or plate member).

V. EXAMPLES

The following examples describe selected aspects and embodiments of the present disclosure related to systems for deforming bone plates and/or plate members thereof after attachment to bone. The components, aspects, steps, and features of the systems described in each of these examples may be combined with one another and with the systems described above, in any suitable combination. These examples are intended for illustration and should not limit the entire scope of the present disclosure.

Example 1. Exemplary Working Models of a Bone Plate and a Bending Tool

Figure 19:
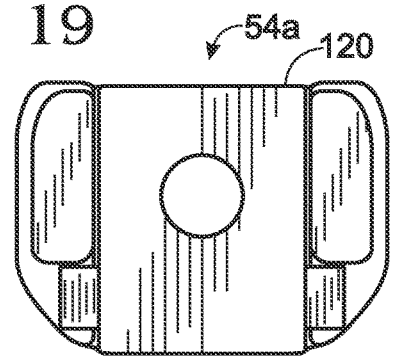
FIG. 19 is a bottom view of a working model of one of the bending tools of FIG. 11.
Figure 20:
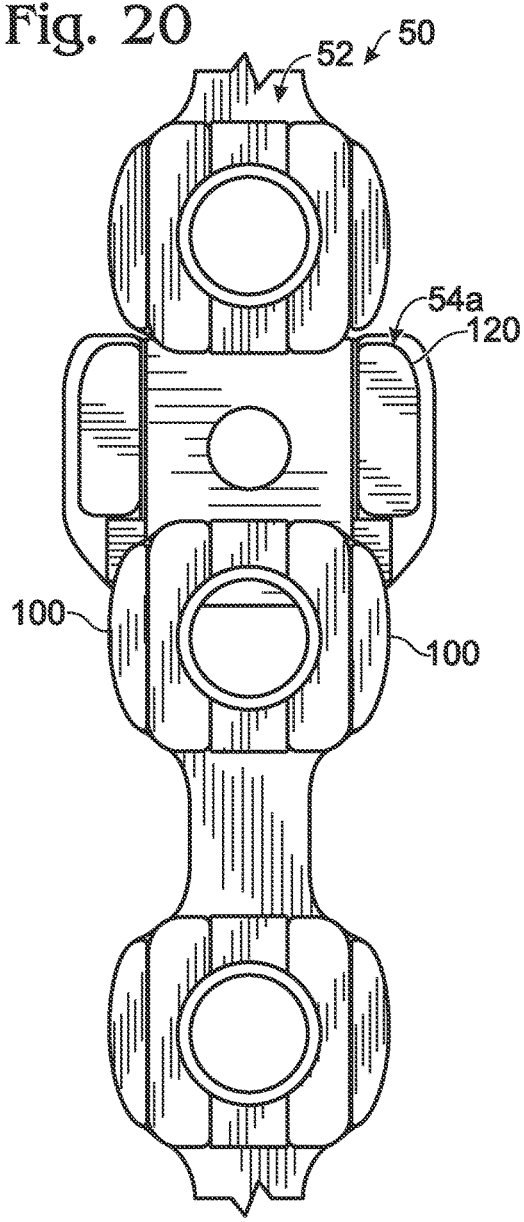
FIG. 20 is a fragmentary bottom view of the bending tool of FIG. 19 aligned for mating with a working model of the bone plate of FIG. 1, but before edge regions of the bone plate have been received in tracks formed in the mating portion of the bending tool.
Figure 21:
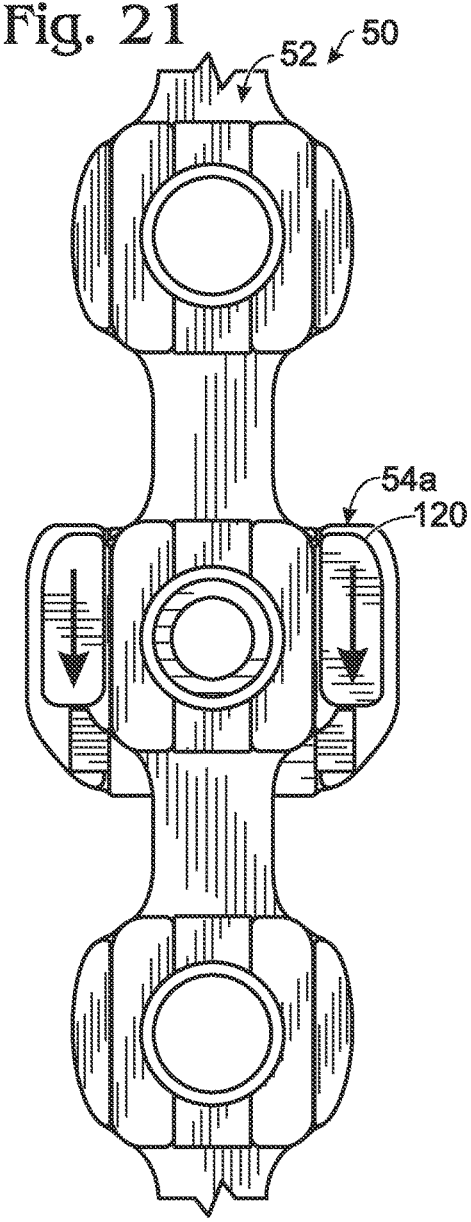
FIG. 21 is a fragmentary bottom view of the bending tool and bone plate of FIG. 20 taken after the tool has been mated with the bone plate by movement of the tool in the direction indicated by a pair of arrows, to operatively associate the tool with the bone plate.

This example describes exemplary working models of bone plate 52 and bending tool 54a; see FIGS. 19-21.

FIG. 19 shows a bottom view of mating portion 120 of tool 54a.

FIG. 20 shows mating portion 120 positioned over an access site of the bone plate and axially aligned with an adjacent association site (including flanges 100) of bone plate 52 before mating.

FIG. 21 shows mating portion 120 mated with an association site of the bone plate and received over flanges 100, by motion of the mating portion as indicated by a pair of arrows.

Example 2. Exemplary Bone Plates and Bending Tools

This example describes additional exemplary bone plates 52 and bending tools for the system of FIG. 1; see FIGS. 22-31.

Figure 22:
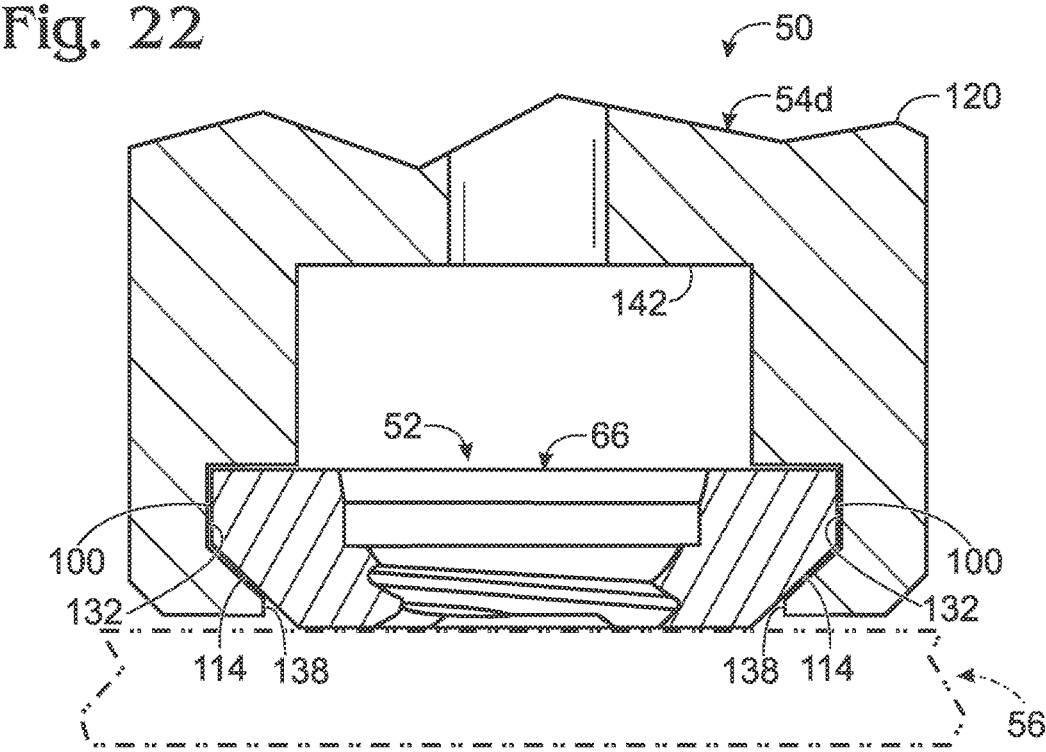
FIGS. 22-25 are fragmentary sectional views of other exemplary in situ bending systems, taken as FIG. 18 with a bending tool and a bone plate of the system operatively associated with one another, and with the bone plate attached to a bone (in phantom outline).

FIG. 22 shows a sectional view of another exemplary bending tool 54d mated with a bone plate 52 at an association site 66. The bone plate has plate flanges 100 each having a beveled underside 114 to form a dovetail shape in cross section. Mating portion 120 of tool 54d has complementary grooves 132 that form tracks to receive plate flanges 100, and has lips 138 (also called tool flanges) that form hooks received under plate flanges 100.

Figure 23:
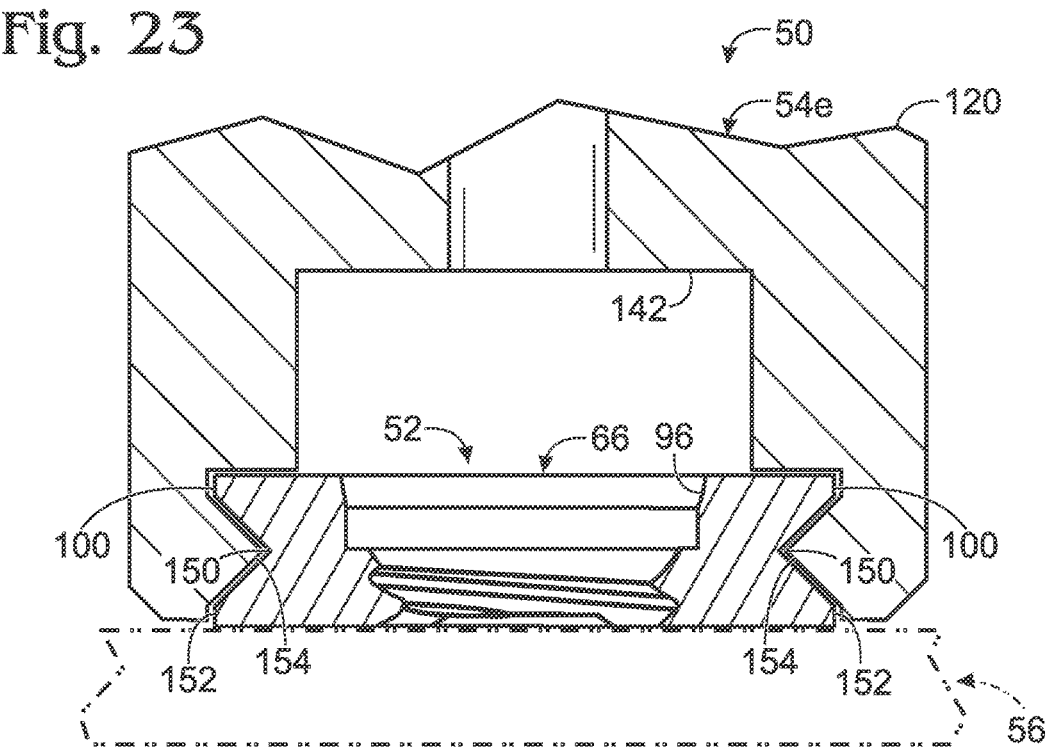
Figure 24:
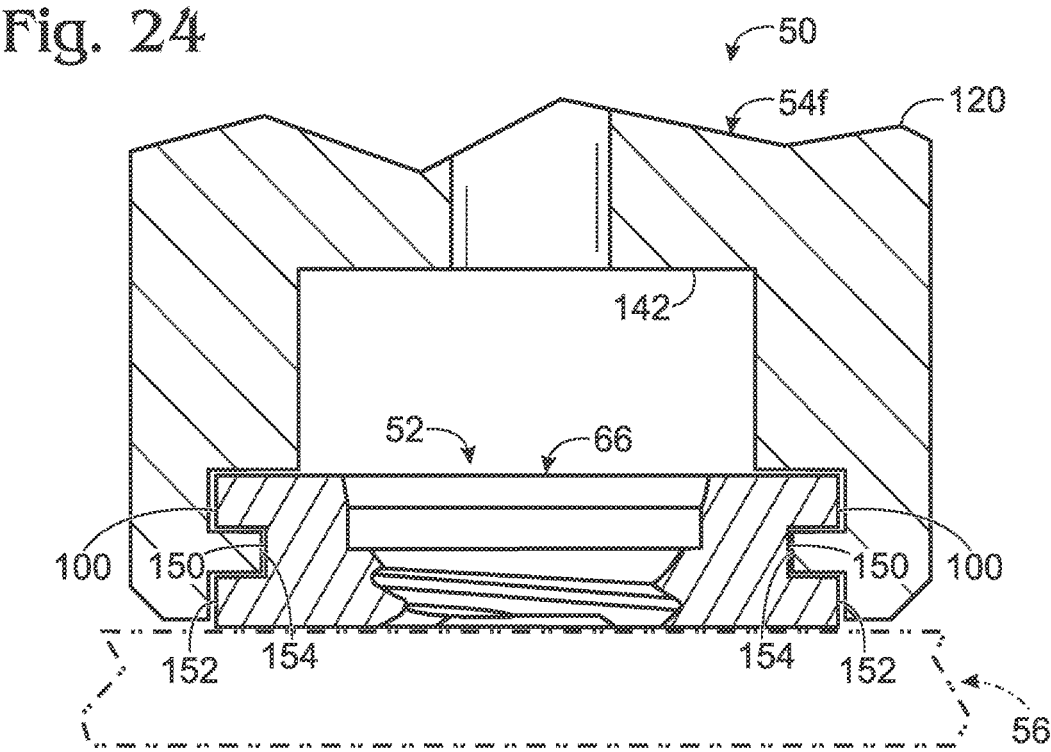
Figure 25:
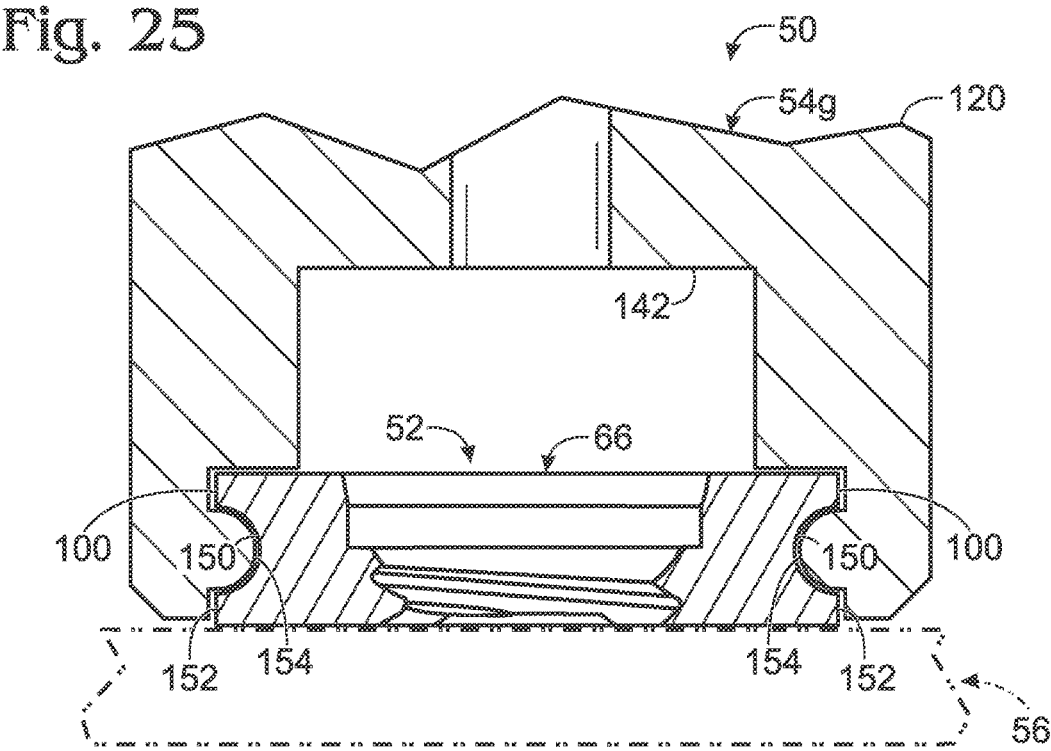

FIGS. 23-25 show sectional views of other exemplary bending tools 54e-g mated with a bone plate 52 at an association site 66. The bone plate has an elongated recess 150 (a groove) extending along each opposite edge region of an association site 66 to create a pair of upper flanges 100 and a pair of lower flanges 152. Each tool 54e-g forms complementary ridges 154 (interchangeably called tool flanges) that fit into elongated recesses 150, such that a region of the tool is located under each upper plate flange 100 of association site 66. Recesses 150 and ridges 154 may have any suitable complementary cross-sectional shape, such as triangular (see FIG. 23), rectangular (see FIG. 24), or circular (see FIG. 25), among others.

FIG. 26 shows a bone plate 52 having flanges 100 each formed by at least two protrusions 156 at each association site 66. Each protrusion 156 may project from a body 98 of the bone plate in a direction orthogonal to a local long axis of the bone plate.

FIG. 27 shows a linear version of bone plate 52 of FIGS. 4-6 having no substantial transverse portion (compare FIGS. 5 and 27).

FIG. 28 shows an angular version of bone plate 52 of FIGS. 4-6 that is L-shaped (compare FIGS. 5 and 28). The longitudinal and transverse portions of the bone plate may be orthogonal or oblique to one another.

FIG. 29 shows a bone plate 52 having undercut flanges 100 extending substantially the entire length of the bone plate. Bending tools may be mated with the bone plate from either end and may be slid to any position within a continuous range of positions along the bone plate.

Figure 30:
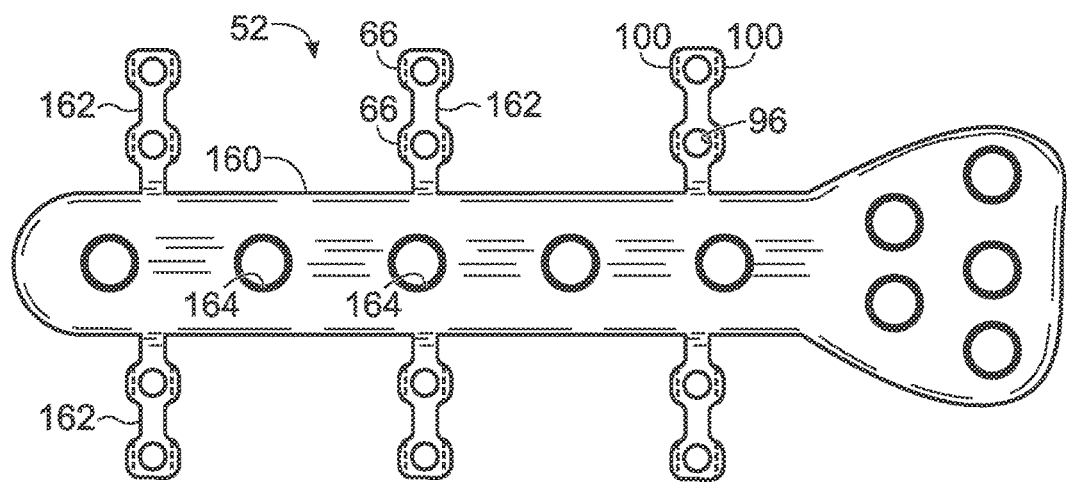
FIG. 30 is a top view of another exemplary bone plate for the bending systems of the present disclosure, with the bone plate having a body and a plurality of appendages formed integrally with the body, and with the appendages each having at least one pair of undercut flanges for operative association with a bending tool.

FIG. 30 shows another exemplary bone plate 52 for the bending systems of the present disclosure. The bone plate has a body 160 (interchangeably called a primary plate member) and a plurality of appendages 162 (interchangeably called ancillary plate members) formed integrally with the body and projecting therefrom (e.g., transversely to the long axis of the body). Each appendage may include at least one or at least a pair of association sites 66 for a bending tool, with each site 66 having a pair of undercut flanges 100 for operative association with the bending tool.

Body 160 may function as a primary fixation structure of the bone plate. The body may be wider and thicker than the appendages and may span one or more primary fractures of a bone (e.g., by extending longitudinally along the bone, such as a femur, tibia, or humerus, among others). The body may define a plurality of openings 164 for receiving fasteners, such as bone screws. Appendages 162 may span secondary fractures of the bone, such as to attach bone plate 52 to smaller bone fragments via the appendages.

Figure 31:
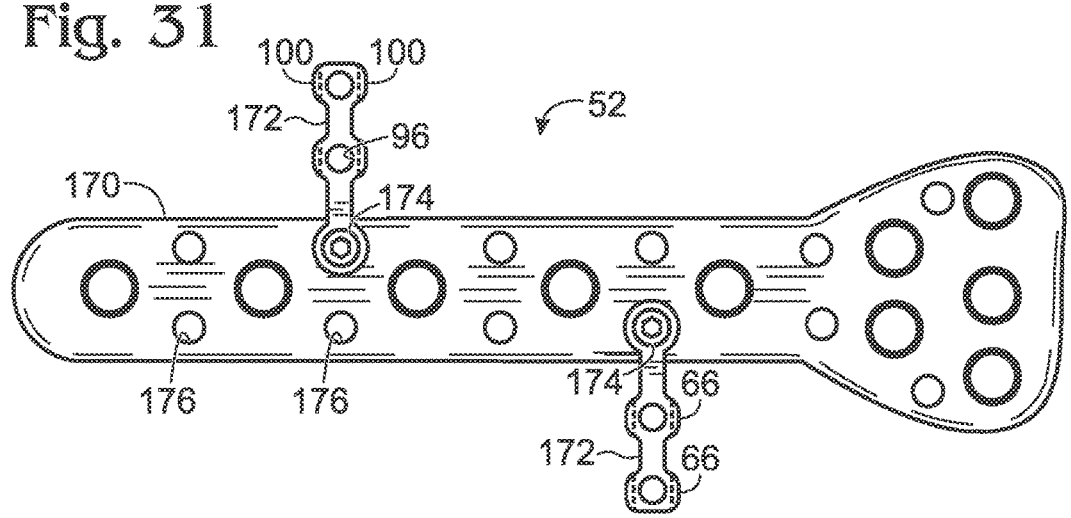
FIG. 31 is a top view of yet another exemplary bone plate for the bending systems of the present disclosure, with the bone plate being an assembly of a body and a plurality of removable appendage attachments (ancillary plate members) formed separately from and fastened to the body with fasteners, and with the attachments each having at least one pair of undercut flanges for operative association with a bending tool.

FIG. 31 shows yet another exemplary bone plate 52 for the bending systems of the present disclosure. The bone plate is an assembly of a primary plate member 170 (interchangeably termed a main plate) and a plurality of removable appendages 172 (interchangeably termed ancillary plate members). Each ancillary plate member may be formed separately from and fastened to the primary plate member with one or more fasteners 174, such as threaded fasteners, at a selectable position. Primary plate member 170 may define a plurality of openings 176 at which each ancillary plate member may be attached with at least one fastener 174, and with the ancillary plate member overlapping the primary plate member and projecting therefrom to increase the footprint of the bone plate assembly on bone. Each opening 176 may or may not have an internal thread.

Primary plate member 170 may be larger and/or stronger than ancillary plate member 172. The primary plate member may be longer, wider, and/or thicker than the ancillary plate member.

The bone plate assembly may include a primary plate member and an ancillary plate member. The ancillary plate member has association sites 66 created by pairs of undercut flanges 100. The ancillary plate member may be disposed over the primary plate member, such that part of the primary plate member is located between the ancillary plate member and bone. At least one of fasteners 174 may extend through an opening of plate member 172 and an opening of plate member 170 and, optionally, into bone. The ancillary plate member may project from an end region of primary plate member 170, to allow capture of smaller bone fragments created by fracture near the end of the bone.

Example 3. Selected Embodiments

This example describes selected embodiments of the present disclosure as a series of indexed paragraphs.

1. A system for deforming a plate member on bone, comprising: (A) a plate member defining a plurality of openings to receive fasteners that attach the plate member to bone and including a pair of undercut flanges formed by opposite edge regions of the plate member; and (B) a bending tool configured to be operatively associated with the plate member after the plate member is attached to bone, with a region of the bending tool positioned under each of the undercut flanges, such that rotation of the bending tool applies a moment to the plate member.

2. The system of paragraph 1, wherein the undercut flanges define a plane, and wherein the bending tool is configured to be operatively associated with the plate member by mating the bending tool and the plate member with one another parallel to the plane.

3. The system of paragraph 1 or 2, wherein the bending tool is configured to be operatively associated with the plate member by mating the bending tool and the plate member with one another longitudinally with respect to the plate member.

4. The system of any of paragraphs 1 to 3, wherein the bending tool forms a pair of tracks, and wherein at least a portion of each flange of the pair of undercut flanges is received by one of the tracks when the bending tool is operatively associated with the plate member.

5. The system of paragraph 4, wherein each track of the pair of tracks includes a groove to receive at least a portion of one of the undercut flanges.

6. The system of any of paragraphs 1 to 5, wherein the bending tool is configured to be operatively associated with the plate member by travel along a mating axis, and wherein the bending tool and/or the plate member includes a stop region that stops the travel when the bending tool is operatively associated with the plate member.

7. The system of any of paragraphs 1 to 6, wherein the bending tool is capable of being operatively associated with the plate member while bone screws operatively occupy each of the openings of the plate member.

8. The system of any of paragraphs 1 to 7, wherein at least one of the openings defined by the plate member is disposed between the pair of undercut flanges, and wherein the at least one opening optionally includes an internal thread.

9. The system of any of paragraphs 1 to 8, wherein the pair of undercut flanges are elongated longitudinally with respect to the plate member and/or project in opposite directions relative to one another, optionally projecting from a body of the plate member.

10. The system of any of paragraphs 1 to 9, wherein the bending tool is configured to be operatively associated with the plate member alternatively at each of a plurality of spaced, discrete association sites along the plate member.

11. The system of paragraph 10, wherein each of the association sites brackets at least one of the openings defined by the plate member.

12. The system of any of paragraphs 1 to 11, wherein the plate member forms pairs of undercut flanges, and wherein the pairs of undercut flanges are spaced from one another along the plate member (i.e., in a longitudinal direction of the plate member).

13. The system of paragraph 12, wherein the plate member is wider at each pair of undercut flanges and narrower between adjacent pairs of undercut flanges.

14. The system of any of paragraphs 1 to 13, wherein the bending tool is a first bending tool, further comprising a second bending tool configured to be operatively associated with the plate member, such that the bending tools can apply opposing moments to the plate member at the same time.

15. The system of any of paragraphs 1 to 14, wherein the plate member is an ancillary plate member, further comprising a primary plate member configured to overlap the ancillary plate member on bone, and wherein, optionally, the ancillary plate member has a smaller average thickness and/or average width than the primary plate member.

16. A system for deforming a plate member on bone, comprising: (A) a plate member having a pair of edge regions located across the plate member from one another; and (B) a bending tool configured to be operatively associated with the pair of edge regions by mating the bending tool and the plate member that displaces the bending tool longitudinally on the plate member.

17. The system of paragraph 16, wherein the plate member includes a body having a bottom surface region, wherein each of the edge regions has an underside that is elevated with respect to the bottom surface region, and wherein the bending tool is configured to be engaged with the underside of each of the edge regions when applying a moment to the plate member.

18. The system of paragraph 16 or 17, wherein the bending tool is configured to be engaged with a top side of the plate member and/or both edge regions when applying a moment to the plate member.

19. A method of fixing bone, the method comprising in any order: (A) attaching a plate member to bone with a plurality of fasteners; (B) operatively mating a bending tool with the plate member by moving the bending tool and plate member relative to one another parallel to a direction of elongation of the plate member; and (C) deforming the plate member at least in part with force applied to the plate member with the bending tool.

20. The method of paragraph 19, wherein the plate member is an ancillary plate member that overlaps a primary plate member, and wherein the ancillary plate member has a smaller average width than the primary plate member.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for deforming a plate member on bone, comprising:

a plate member defining a plurality of openings to receive fasteners that attach the plate member to bone and including a pair of undercut flanges formed by opposite edge regions of the plate member; and a bending tool configured to be operatively associated with the plate member after the plate member is attached to bone, with a region of the bending tool positioned under each of the undercut flanges, such that rotation of the bending tool applies a moment to the plate member.

2. The system of claim 1, wherein the undercut flanges define a plane, and wherein the bending tool is configured to be operatively associated with the plate member by mating the bending tool and the plate member with one another parallel to the plane.

3. The system of claim 1, wherein the bending tool is configured to be operatively associated with the plate member by mating the bending tool and the plate member with one another longitudinally with respect to the plate member.

4. The system of claim 1, wherein the bending tool forms a pair of tracks, and wherein at least a portion of each flange of the pair of undercut flanges is received by one of the tracks when the bending tool is operatively associated with the plate member.

5. The system of claim 4, wherein each track of the pair of tracks includes a groove to receive at least a portion of one of the undercut flanges.

6. The system of claim 1, wherein the bending tool is configured to be operatively associated with the plate member by travel along a mating axis, and wherein the bending tool and/or the plate member includes a stop region that stops the travel when the bending tool is operatively associated with the plate member.

7. The system of claim 1, wherein the bending tool is capable of being operatively associated with the plate member while bone screws operatively occupy each of the openings of the plate member.

8. The system of claim 1, wherein at least one of the openings defined by the plate member is disposed between the pair of undercut flanges.

9. The system of claim 1, wherein the pair of undercut flanges are elongated longitudinally with respect to the plate member and project in opposite directions relative to one another.

10. The system of claim 1, wherein the bending tool is configured to be operatively associated with the plate member alternatively at each of a plurality of spaced, discrete association sites along the plate member.

11. The system of claim 10, wherein each of the association sites brackets at least one of the openings defined by the plate member.

12. The system of claim 1, wherein the plate member forms pairs of undercut flanges, and wherein the pairs of undercut flanges are spaced from one another along the plate member.

13. The system of claim 12, wherein the plate member is wider at each pair of undercut flanges and narrower between adjacent pairs of undercut flanges.

14. The system of claim 1, wherein the bending tool is a first bending tool, further comprising a second bending tool configured to be operatively associated with the plate member, such that the bending tools can apply opposing moments to the plate member at the same time.

15. The system of claim 1, wherein the plate member is an ancillary plate member, further comprising a primary plate member configured to overlap the ancillary plate member on bone.

16. A system for deforming a plate member on bone, comprising:

a plate member having a pair of edge regions located across the plate member from one another; and a bending tool configured to be operatively associated with the pair of edge regions by mating the bending tool and the plate member with one another, wherein the plate member includes a body having a bottom surface region, wherein each of the edge regions has an underside that is elevated with respect to the bottom surface region, and wherein the bending tool is configured to be engaged with the underside of each of the edge regions when applying a moment to the plate member.

17. The system of claim 16, wherein the bending tool is configured to be engaged with a top side of the plate member when applying the moment to the plate member.

18. A method of fixing bone, the method comprising in any order:

attaching a plate member to hone with a plurality of fasteners, the plate member having a pair of edge regions located across the plate member from one another;

operatively mating a bending tool with the plate member by moving the bending tool and plate member relative to one another parallel to a direction of elongation of the plate member; and deforming the plate member at least in part with force applied to the plate member with the bending tool, wherein the plate member includes a body having a bottom surface region, wherein each of the edge regions has an underside that is elevated with respect to the bottom surface region, and wherein the bending tool is configured to be engaged with the underside of each of the edge regions when applying a moment to the plate member.

19. The method of claim 18, wherein the plate member is an ancillary plate member that overlaps a primary plate member, and wherein the ancillary plate member has a smaller average width than the primary plate member.

* * * * *